US008404661B2

(12) United States Patent
Conti et al.

(10) Patent No.: US 8,404,661 B2
(45) Date of Patent: *Mar. 26, 2013

(54) WOUND-HEALING PHARMACEUTICAL COMPOSITIONS IN THE FORM OF A CREAM BASED ON AMINO ACIDS AND SODIUM HYALURONATE

(75) Inventors: Franco Conti, Milan (IT); Edoardo Carlo Maria Conti, legal representative, Milan (IT); Federico Giovanni Maria Conti, legal representative, Milan (IT); Isabella Arborio Mella, legal representative, Milan (IT); Francesco Saverio Dioguardi, Milan (IT)

(73) Assignee: Professional Dietetics S.R.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 12/954,840

(22) Filed: Nov. 26, 2010

(65) Prior Publication Data

US 2011/0071105 A1 Mar. 24, 2011

Related U.S. Application Data

(63) Continuation of application No. 12/091,462, filed as application No. PCT/EP2006/009966 on Oct. 16, 2006, now abandoned.

(30) Foreign Application Priority Data

Oct. 26, 2005 (IT) .............................. MI2005A2035

(51) Int. Cl.
*A61K 31/715* (2006.01)
*A61P 17/02* (2006.01)

(52) U.S. Cl. ......................................................... 514/55
(58) Field of Classification Search ........................ None
See application file for complete search history.

(56) References Cited

U.S. PATENT DOCUMENTS

| 6,645,948 B2 * | 11/2003 | Petito et al. ................. 514/62 |
| 2002/0013359 A1 * | 1/2002 | Dioguardi ...................... 514/423 |
| 2003/0021834 A1 * | 1/2003 | Petito ............................ 424/445 |
| 2008/0287392 A1 | 11/2008 | Conti |

FOREIGN PATENT DOCUMENTS

WO WO03/013487 * 2/2003

OTHER PUBLICATIONS

Berge, S. M. et al., Journal of Pharmaceutical Sciences, "Pharmaceutical Salts", Jan. 1977, vol. 66, No. 1-19.*
Eastoe, J. E., Biochemical Journal, "The amino acid composition of mammalian collagen and gelatin", Dec. 1955, vol. 61, No. 4, pp. 589-600.*
Kuchel, P. W. et al., Schaum's Outline of Theory and Problems of Biochemistry, 2nd Edition, McGraw-Hill, copyright 1998, "Chapter 3: Amino Acids and Peptides", pp. 53-56 and 63-65.*
Notice of Abandonment issued for U.S. Appl. No. 12/091,462, filed Apr. 24, 2008 in the name of Solartium LLC; mail date: Feb. 23, 2011.
Restriction Requirement issued for U.S. Appl. No. 12/091,481, filed Apr. 24, 2008 in the name of Solartium LLC; mail date: Dec. 30, 2009.
Non-Final Office Action issued for U.S. Appl. No. 12/091,481, filed Apr. 24, 2008 in the name of Solartium LLC; mail date: Jun. 16, 2010.
Notice of Abandonment issued for U.S. Appl. No. 12/091,481, filed Apr. 24, 2008 in the name of Solartium LLC; mail date: Mar. 1, 2011.
Non-Final Office Action issued for U.S. Appl. No. 12/091,551, filed Apr. 25, 2008 in the name of Solartium LLC; mail date: Jun. 10, 2010.
Notice of Abandonment issued for U.S. Appl. No. 12/091,551, filed Apr. 25, 2008 in the name of Solartium LLC; mail date: Feb. 11, 2011.
Ashcroft, G.S. et al., Topical Estrogen Accelerates Cutaneous Wound Healing in Aged Humans Associated with an Altered Inflammatory Response, *American Journal of Pathology*, Oct. 1999, vol. 155, No. 4, pp. 1137-1146.
Greenhalgh, D.G. et al., PDGF and FGF Stimulate Wound Healing in the Genetically Diabetic Mouse, *American Journal of Pathology*, Jun. 1990, vol. 136, No. 6, pp. 1235-1246.
Ashcroft, G.S. et al., Mice lacking Smad3 show accelerated would healing and an impaired local inflammatory response, *Nature Cell Biology*, Sep. 1999, vol. 1, pp. 260-266.
El Ghalbzouri, A. et al., Fibroblasts facilitate re-epithelialization in wounded human skin equivalents, *Laboratory investigation*, 2004, vol. 84, 102-112.
Di Colandrea, T. et al., Epidermal Expression of Collagenase Delays Wound-Healing in Transgenic Mice, *The Society for Investigative Dermatology, Inc.*, 1998, pp. 1029-1033.
Kapoor, M. et al., GSK-3β in mouse fibroblasts controls wound healing and fibrosis through an endothelin-1-dependent mechanism, *The Journal of Clinical Investigation*, Oct. 2008, vol. 118, No. 10, pp. 3279-3290.
Hu, C. et al., Basic fibroblast growth factor stimulates epithelial cell growth and epithelial wound healing in canine corneas, *Veterinary Ophthalmology*, 2009, vol. 12, No. 3, pp. 170-175.
Unemori, E.N. et al., Interleukin-1 and transforming growth factor-alpha: synergistic stimulation of metalloproteinases, PGE2, and proliferation in human fibroblasts, *Exp. Cell Res.*, Feb. 1994, vol. 210, No. 2, p. 166 (Abstract).
Brown, R.L. et al., PDGF and TGF-α Act Synergistically to Improve Wound Healing in the Genetically Diabetic Mouse, *Journal of Surgical Research*, 1994, vol. 56, pp. 562-570.
Lee et al. Electroporatic Delivery of TGF-b1 Gene Works Synergistically with Electric Therapy to Enhance Diabetic Wound Healing in db/db Mice *J. Invest Dermatol.* 2004, 123, 791-798.
Restriction Requirement issued for U.S. Appl. No. 12/964,522, filed Dec. 9, 2010 in the name of Franco Conti; mail date: Jul. 27, 2012.
Non-Final Office Action issued for U.S. Appl. No. 12/964,522, filed Dec. 9, 2010 in the name of Franco Conti; mail date: Sep. 13, 2012.
Restriction Requirement issued for U.S. Appl. No. 12/964,419, filed Dec. 9, 2010 in the name of Franco Conti; mail date: Mar. 13, 2012.
Non-Final Office Action issued for U.S. Appl. No. 12/964,419, filed Dec. 9, 2010 in the name of Franco Conti; mail date: Jun. 19, 2012.
Ashcroft, G.S. et al., Mice lacking Smad3 show accelerated wound healing and an impaired local inflammatory response, *Nature Cell Biology*, Sep. 1999, vol. 1, pp. 260-266.
El Ghalbzouri, A. et al., Fibroblasts facilitate re-epithelialization in wounded human skin equivalents, *Laboratory Investigation*, 2004, vol. 84, pp. 1-11.
Colandrea, T.D. et al., Epidermal Expression of Collagenase Delays Wound-Healing in Transgenic Mice, *The Society for Investigative Dermatology, Inc.*, 1998, pp. 1029-1033.

(Continued)

*Primary Examiner* — Layla Bland
*Assistant Examiner* — Bahar Craigo
(74) *Attorney, Agent, or Firm* — Steinfl & Bruno, LLP

(57) ABSTRACT

This invention relates to wound-healing pharmaceutical or cosmetic (anti-skin aging) compositions in the form of a cream based on amino acids and sodium hyaluronate.

12 Claims, No Drawings

OTHER PUBLICATIONS

Unemori, E.N. et al., Interleukin-1 and transforming growth factor-alpha: synergistic stimulation of metalloproteinases, PGE2, and proliferation in human fibroblasts, Exp. Cell Res., Feb. 1994, vol. 210, No. 2, pp. 166-171.

Lee, P-Y. et al., Electroporatic Delivery of TGF-β1 Gene Works Synergistically with Electric Therapy to Enhance Diabetic Wound Healing in db/db Mice, *The Society for Investigative Dermatology, Inc.*, 2004, pp. 791-798.

Cattaneo MG, Cappellini E, Benfante R, Ragni M, Omodeo-Salè F, Nisoli E, Borgese N, Vicentini LM Chronic deficiency of nitric oxide affects hypoxia inducible factor-1α (HIF-1α) stability and migration in human endothelial cells. *PLoS One*. 2011; 6(12):e29680. Epub Dec. 27, 2011.

Valerio A et al., Glycogen synthase kinase-3 inhibition reduces ischemic cerebral damage, restores impaired mitochondrial biogenesis and prevents ROS production. *J Neurochem*. Mar. 2011; 116(6):1148-59. doi: 10.1111/j.1471-4159.2011.07171.x. Epub Jan. 28, 2011.

D'Antona G, et al., Branched-chain amino acid supplementation promotes survival and supports cardiac and skeletal muscle mitochondrial biogenesis in middle-aged mice. *Cell Metab*. Oct. 6, 2010; 12(4):362-72.

Tedesco L, et al., Cannabinoid receptor stimulation impairs mitochondrial biogenesis in mouse white adipose tissue, muscle, and liver: the role of eNOS, p38 MAPK, and AMPK pathways. *Diabetes*. Nov. 2010; 59(11):2826-36. Epub Aug. 25, 2010.

Funicello M, et al., Cathepsin K null mice show reduced adiposity during the rapid accumulation of fat stores. *PLoS ONE*. 2007 Aug. 1, 2007; 2(1).

de Lange P., et al., Differential 3,5,3'-triiodothyronine-mediated regulation of uncoupling protein 3 transcription: role of Fatty acids. *Endocrinology*. Aug. 2007; 148(8):4064-72.

de Lange P, Farina P, Moreno M, Ragni M, Lombardi A, Silvestri E, Burrone L, Lanni A, Goglia F. Sequential changes in the signal transduction responses of skeletal muscle following food deprivation *FASEB J*. Dec. 2006; 20(14):2579-81.

Silvestri E, de Lange P, Moreno M, Lombardi A, Ragni M, Feola A, Schiavo L, Goglia F, Lanni A Fenofibrate activates the biochemical pathways and the de novo expression of genes related to lipid handling and uncoupling protein-3 functions in liver of normal rats. *Biochim Biophys Acta*. May-Jun. 2006; 1757(5-6):486-95.

Lanni A, Moreno M, Lombardi A, de Lange P, Silvestri E, Ragni M, Farina P, Baccari GC, Fallahi P, Antonelli A, Goglia F. 3,5-diiodo-L-thyronine powerfully reduces adiposity in rats by increasing the burning of fats *FASEB J*. Sep. 2005; 19(11):1552-4. Epub Jul. 12, 2005.

Silvestri E, Moreno M, Lombardi A, Ragni M, de Lange P, Alexson SE, Lanni A, Goglia F Thyroid-hormone effects on putative biochemical pathways involved in UCP3 activation in rat skeletal muscle mitochondria. FEBS Lett. Mar. 14, 2005; 579(7):1639-45.

De Lange P., Ragni M., Silvestri E., Moreno M., Schiavo L., Lombardi A., Farina P., Feola A., Goglia F., Lanni A. Combined cDNA array/ RT-PCR analysis of the gene expression profile in rat gastrocnemius muscle: relation to its adaptive function in energy metabolism during fasting. *FASEB J*. Feb. 2004; 18(2):350-2.

Moreno M., Lombardi A., de Lange P., Silvestri E., Ragni M., Lanni A., Goglia F. Fasting, lipid metabolism, and triiodothyronine in rat gastrocnemius muscle; interrelated roles of uncoupling protein 3, mitochondrial thioesterase, and coenzyme Q. *FASEB J*. Jun. 2003; 17(9):1112-4.

Albina et al., Temporal expression of different pathways of 1-arginine metabolism in healing wounds, *J Immunol* vol. 144, pp. 3877-3880, 1990.

Eming SA et al., Regulation of angiogenesis: Wound healing as a model, *Progress in Histochemistry and Cytochemistry*, vol. 42(3): 115-170, Dec. 10, 2007.

Frank et al., Induction of Inducible Nitric Oxide Synthase and its Coressponding Tetrahydrobiopterin-Cofactor-Synthesizing Enzyme GTP-Cyclohydrolase I During Cutaneous Wound Repair, *The Society for Investigative Dermatology, Inc., J Invest Dermatol* 111: 1058, 1998.

Ring BD et al., Systemically and Topically Administered Leptin Both Accelerate Wound Healing in Diabetic ob/ob Mice, *Endocrinology* vol. 141(1): 446-449, 2000.

Roberts et al., Transforming growth factor type β: Rapid induction of fibrosis and angiogenesis in vivo and stimulation of collagen formation in vitro, *Proc Nat Acad Sci* USA 83: 4167-4171, 1986.

Schwentker et al., Nitric oxide and wound repair: role of cytokines?, *Nitric Oxide* vol. 7, Issue 1, pp. 1-10, Aug. 2002.

Steed D.L., The Role of Growth Factors in Wound Healing, *Surgical Clinics of North America*, vol. 77, pp. 575-586, 1997.

Vodovotz et al., Mechanisms of Suppresison of Macrophage Nitric Oxide Release by Transforming Growth Factor β, *J Exp Med* 178: 605-613, 1993.

Witte, M.B. et al., Role of nitric oxide in wound repair, *Am J Surg*. vol. 183, pp. 406-412, 2002.

Yamasaki et al., Reversal of Impaired Wound Repair iniNOS-deficient Mice by Topical Adenoviral-mediated iNOS Gene Transfer, *J Clin Investigation, Inc.*, vol. 101, No. 5,pp. 967, 1998.

Corsetti G, D'Antona G, Bianchi R, Rezzani R. Topic application of essential aminoacids dressing improves wound healing in old rats. *Atti del Congresso della Societa Italiana di Anatomia e Istologia*, Verona, 2008.

Grose R, Martin P. Parallels between wound repair and morphogenesis in the embryo. *Semin Cell Dev Biol* 10: 395-404, 1999.

Harty M, Neff A W, King MW, Mescher AL. Regeneration or scarring: an immunologic perspective. *Dev Dyn* 226: 268-279, 2003.

Klyce S. Electrical profiles in the corneal epithelium. J Phisiol226: 407-429, 1972. Li DQ, Tseng SC. Three patterns of cytokine expression potentially involved in epithelialfibroblast interactions of human ocular surface. *J Cell Physiol* 163: 61-70, 1995.

Three patterns of cytokine expression potentially involved in epithelialfibroblast interactions of human ocular surface. *J Cell Physiol* 163: 61-70, 1995.

Lu L, Reinach PS, WY Kao. Corneal epithelium wound healing. *Exp Biol and Med* 226(7). 653-664, 2001.

Nishimura T, Toda S, Mitsumoto T, Oono S, Suhigara H. Effects of hepatocyte growth factor, transforming growth factor-beta 1 and epidermal growth factor on bovine corneal epithelial cells under epithelial-keratinocyte interaction in reconstruction culture. *Exp Eye Res* 66: 105-116, 1998.

Veno M, et al., Accelerated wound healing of alkali-burned corneas in MRL mice is associated with a reduced inflammatory signature. *Invest Ophthalm & Visual Sci* 46 (11): 4097-4106, 2005.

Whitby DJ, Longaker MT, Harrison MR, Adzick NS, Ferguson MW. Rapid epithelisation of foetal wounds is associated with the early deposition of tenascin. *J Cell Sci* 99:586, 1991.

\* cited by examiner ized area of up to 6 cm² and a maximum depth of 1 cm presented complete healing, 14 were definitely improved, and only 8 had no healing effect. The final 38 patients, suffering from post-phlebitic ulcers, presented complete healing in 12 cases and marked improvement with a reduction of the de-epithelialised area of over 70% in 16 cases, while the remaining 10 patients did not present any evident results.

WOUND-HEALING PHARMACEUTICAL COMPOSITIONS IN THE FORM OF A CREAM BASED ON AMINO ACIDS AND SODIUM HYALURONATE

CROSS REFERENCE TO RELATED APPLICATIONS

The present application is a continuation application of U.S. patent application Ser. No. 12/091,462 filed on Apr. 24, 2008 and incorporated herein by reference in its entirety, which is the national stage entry of PCT/EP2006/009966 filed on Oct. 16, 2006 which, in turn, claims priority to Italian Patent Application MI2005A002035 filed on Oct. 26, 2005. The present application may also be related to U.S. patent application Ser. No. 12/091,481 filed on Apr. 24, 2008 and U.S. patent application Ser. No. 12/091,551 filed on Apr. 25, 2008.

FIELD OF INVENTION

The present invention relates to wound-healing pharmaceutical compositions in the form of a cream based on amino acids and sodium hyaluronate.

PRIOR ART

In the absence of suitable preventive actions, patients who are paralysed or bedridden for long periods are liable to ischaemic necrosis and ulceration of the tissues covering projecting bones, especially in the sacral, ischial, malleolar, heel and great trochanter regions.

Bedsores and chronic ulcerous wounds are usually treated with gentle massage to restore the circulation, possibly with mechanical removal of the necrotic tissue and cleansing with soap (which can cause oedema or dehydration), or with hydrophilic polymers, hydrogen peroxide or alcohol rubs (which can cause damage because the removal of the fats in the cutaneous tissue dries and cracks the skin).

Serious burns also require debridement of the affected area and removal of necrotic tissue.

DESCRIPTION OF THE INVENTION

It has now been found that the combination of some amino acids with sodium hyaluronate is particularly effective in promoting the process of cell reintegration which forms the basis for fast wound-healing, aiding the reconstruction of connective tissue and the consequent regeneration of epithelial cells.

The invention therefore relates to wound-healing pharmaceutical compositions in the form of a cream, containing, as active ingredient, a combination of:
 a) glycine and proline;
 b) sodium hyaluronate; and possibly;
 c) lysine and leucine.

More particularly, the compositions according to the invention contain glycine, L-proline and sodium hyaluronate, and possibly L-lysine in hydrochloride form, and L-leucine.

The compositions according to the invention have proved a surprising adjuvant effect in promoting the healing of ordinary wounds, including surgical wounds, vaginal and rectal lesions, buccal wounds and lesions, including those from dental surgery, as well as wounds which cannot be stitched and have seriously damaged the derrnis, including loss of skin substance, such as chronic ulcerous wounds, serious burns and bedsores.

The compositions of the invention promote the elimination of necrotic tissue, thus facilitating more rapid regeneration of the tissues, and maintain the ideal humidity conditions to aid re-epithelialisation of the skin lesions, at the same time preventing the spread of germs.

The compositions of the invention are also useful for the treatment and/or prevention of skin aging.

The compositions of the invention will be applied to the affected area after removing any foreign material by thorough washing with a hydrogen peroxide solution or saline solution, and removing any excess blood with sterile gauze.

For the vaginal and rectal administration, the compositions of the invention will be applied to the affected area possibly after suitable cleansing of the affected area with appropriate cleansing formulations.

The compositions according to the invention will contain the various active ingredients within the following percentage ranges by weight:
 glycine 0.5 to 2%;
 L-proline: 0.2 to 1.5%;
 sodium hyaluronate: 0.5 to 3%; and possibly
 L-lysine hydrochloride: 0.05 to 1%;
 L-leucine: 0.05 to 0.3%.

According to a preferred aspect, the compositions according to the invention will contain the various active ingredients in the following percentages by weight:
 glycine 1%;
 L-proline: 0.75%;
 sodium hyaluronate.: 1.33%; and possibly
 L-lysine hydrochloride: 0.1%;
 L-leucine: 0.15%.

The compositions according to the invention can be formulated suitably for the topical administration in the form of a cream, and prepared according to conventional methods well known in pharmaceutical technology, such as those described in Remington's Pharmaceutical Handbook, Mack Publishing Co., N.Y., USA, using excipients, solubilisers, emollients, stabilisers, emulsifiers, pH regulators, and preservatives acceptable for their final use.

Pharmacological Trial

The ability of the compositions of the invention to heal chronic sores in elderly patients, diabetics and patients with vascular disease was evaluated.

In particular, 32 elderly patients suffering from bedsores, 31 Type II diabetics with ulcers extending to the lower limbs, and 38 patients with post-phlebitic ulcers were evaluated.

The treatment was given three/four times a week, depending on the severity of the lesions, by spreading the cream on the wound.

The bedsores had to have a de-epithelialised area of over 10 cm² which had already been treated by conventional means for over 4 months, without any evident results. The type of bandage was irrelevant.

The sore was clinically evaluated and photographed before treatment in the fourth and eighth weeks of the trial. "Healing" was defined as closing of the wounds, and "improvement" as a reduction in size of the treated area exceeding 70% of the initial area.

By the fourth week of treatment 20 patients showed an improvement, namely a reduction in size of the sore of over 70%, and 3 were completely healed; by the end of the observation period (8th week), 16 patients were healed, 12 had improved and 4 patients presented a reduction of under 50% in the de-epithelialised area, Of the 31 diabetics with ulcers of various areas and depths, which had already been treated unsuccessfully for at least four months prior to our study, 9 were healed after four weeks' treatment, and another 16 no longer presented ulcerated areas by the end of treatment period. In 6 particularly serious cases there was an improvement, but the sore was still present by the end of the 8th week of treatment.

In patients with post-phlebitic ulcers who had already undergone conventional treatment for at least two months with no result, the administration of the cream compositions according to the invention led to healing within one month in 15 patients and by the end of treatment (8th week) in another 19 patients, making a total of 34 out of 38 treated.

In conclusion, in the case of bedsores, diabetic and post-phlebitic skin ulcers, the cream compositions according to the invention obtained healing indexes (expressed as % improvement) exceeding 80% by comparison with conventional treatment The compositions of the invention also proved to be very effective in the treatment of ordinary wounds, including surgical wounds, vaginal and rectal lesions as well as in the treatment and/or prevention of skin aging.

The compositions of the invention also proved to be very effective in the treatment of buccal wounds and lesions, including those from dental surgery.

An example of a cream formulation according to the invention is set out below.

EXAMPLE

| INGREDIENTS | % Composition |
|---|---|
| Purified water | 82.27 |
| Sodium hyaluronate | 1.33 |
| Glycine | 1.00 |
| L-Proline | 0.75 |
| L-Leucine | 0.15 |
| L-Lysine HCl | 0.10 |
| Cetyl stearyl octanoate (Saboderm CSO) | 6.00 |
| Acrylic acid and vinyl ester copolymer (Stabylen30) | 0.30 |
| Cetyl stearyl alcohol (Lanette O) | 4.00 |
| Potassium cetyl phosphate (Amphisol K) | 3.00 |
| Imidazolidinyl urea (Preservative G) | 0.30 |
| Phenoxyethanol-parabens (Sepicide Hb2) | 0.60 |
| 32% Sodium hydroxide | 0.20 |

The invention claimed:

1. A pharmaceutical composition in form of a cream, the pharmaceutical composition containing as active ingredient a combination of:
   a) glycine and proline; and
   b) sodium hyaluronate
wherein glycine, L-proline and sodium hyaluronate are comprised within the following percentage ranges by weight:
   glycine 0.5 to 2%;
   L-proline: 0.2 to 1.5%; and
   sodium hyaluronate: 0.5 to 3%.

2. The pharmaceutical composition of claim 1, the composition further comprising as active ingredient:
   c) lysine hydrochloride and leucine.

3. The pharmaceutical composition of claim 2, wherein lysine hydrochloride is L-lysine hydrochloride, leucine is L-leucine, and wherein L-lysine and L-leucine are comprised within the following percentage ranges by weight:
   L-lysine hydrochloride: 0.05 to 1%; and
   L-leucine: 0.05 to 0.3%.

4. The pharmaceutical composition of claim 1, wherein proline is L-proline, and wherein glycine, L-proline and sodium hyaluronate have the following percentage ranges by weight:
   glycine 1%;
   L-proline: 0.75%; and
   sodium hyaluronate: 1.33%.

5. The pharmaceutical composition of claim 2, wherein lysine hydrochloride is L-lysine hydrochloride, leucine is L-leucine and wherein L-lysine and L-leucine have the following percentage ranges by weight:
   L-lysine hydrochloride 0.1%; and
   L-leucine: 0.15%.

6. A method for treating a wound in a biological tissue, the method comprising
   administering to the biological tissue a medicament in form of a cream, the medicament comprising as active ingredient the pharmaceutical composition of claim 1.

7. The method of claim 6, wherein the medicament further comprises lysine hydrochloride and leucine.

8. The method of claim 6, wherein, the wound is a surgical wound, a vaginal lesion, a rectal lesion, a buccal wound or lesion, a wound from dental surgery, a chronic ulcerous wound, a serious burn, a bedsore or a wound associated with skin aging.

9. A method to promote regeneration of epithelial cells of a vaginal or rectal tissue, the method comprising
   administering to the vaginal or rectal tissue a medicament in form of a cream for vaginal or rectal administration, the medicament comprising as active ingredient the pharmaceutical composition of claim 1.

10. The method of claim 9, wherein the medicament further comprises lysine hydrochloride and leucine.

11. A method to promote regeneration of epithelial cells of a buccal tissue, the method comprising administering to the buccal tissue a medicament in form of a cream for buccal administration, the medicament comprising as active ingredient the pharmaceutical composition of claim 1.

12. The method of claim 11, wherein the medicament further comprises lysine hydrochloride and leucine.

* * * * *